United States Patent

Wentler

[11] 4,000,092
[45] Dec. 28, 1976

[54] CLEANING COMPOSITIONS

[75] Inventor: George Edward Wentler, West Chester, Ohio

[73] Assignee: The Procter & Gamble Company, Cincinnati, Ohio

[22] Filed: Apr. 2, 1975

[21] Appl. No.: 562,308

[52] U.S. Cl. .............................. 252/526; 252/542; 252/545; 252/546; 260/501.12

[51] Int. Cl.² ............... C11D 3/066; C11D 1/18

[58] Field of Search ............ 252/542, 546, DIG. 1, 252/547, 545, 526; 260/501.12, 458

[56] References Cited

UNITED STATES PATENTS

| | | | |
|---|---|---|---|
| 2,781,390 | 2/1957 | Mannheimer | 260/458 |
| 3,280,179 | 10/1968 | Ernst | 260/501.12 |
| 3,359,275 | 12/1967 | Mannheimer | 252/542 X |
| 3,424,545 | 1/1969 | Bauman | 252/89 |
| 3,449,430 | 6/1969 | Dohr et al. | 252/547 X |
| 3,452,066 | 6/1969 | Mannheimer | 252/550 X |
| 3,503,890 | 3/1970 | Davisson et al. | 252/547 X |
| 3,505,396 | 4/1970 | Sanders et al. | 252/545 X |
| 3,619,115 | 11/1971 | Diehl et al. | 8/137 |
| 3,668,240 | 6/1972 | Barbera | 260/501.12 |
| 3,684,427 | 8/1972 | Walz et al. | 8/26 |
| 3,769,311 | 10/1973 | Armstrong et al. | 252/545 X |
| 3,813,349 | 5/1974 | Wolfson | 252/526 |
| 3,925,262 | 12/1975 | Laughlin et al. | 252/545 |
| 3,929,678 | 12/1975 | Laughlin et al. | 252/526 |

*Primary Examiner*—Thomas J. Herbert, Jr.
*Attorney, Agent, or Firm*—Charles R. Wilson; Jerry J. Yetter; Richard C. Witte

[57] ABSTRACT

Detergent compositions comprising surfactants, optional builders, and zwitterionic co-surfactants of the formula

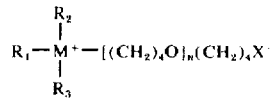

wherein $R_1$, $R_2$ and $R_3$ are hydrocarbon groups, $n$ is 1 to 20, M is nitrogen or phosphorus, and X is, for example, sulfate or sulfonate.

30 Claims, No Drawings

CLEANING COMPOSITIONS

BACKGROUND OF THE INVENTION

This invention relates to fully formulated detergent compositions comprising a mixture of one or more detersive surfactants and a zwitterionic tetramethylene oxide (TMO) compound. More particularly, this invention encompasses detergent compositions comprising mixtures of one or more detersive surfactants with novel zwitterionic co-surfactants characterized by a particular placement and number of TMO groups and particular hydrophobic groups. The combination of these ingredients provides superior detergency performance over a broad spectrum of soils and with a wide variety of fabric types.

The use of zwitterionic compounds (i.e., the so-called "internally neutralized" surface active compounds having both positive and negative charge centers) in fully formulated laundry detergent compositions is known. In contrast with many prior art detergents, the compositions herein employ zwitterionic compounds having a TMO substituent which provides both charge separation and hydration interposed between the oppositely-charged centers of the molecule as a co-surfactant. The TMO-zwitterionics are particularly useful for removing clay and oily soils from fabrics.

The importance of the present invention resides not only in the superior cleaning performance of the disclosed compositions, but also in the flexibility in the choice of surfactants and the favorable economics of the compositions. For example, the TMO moiety can be introduced into the instant zwitterionic co-surfactants using tetrahydrofuran as a precursor. Tetrahydrofuran, in turn, is available from plant by-products such as corncobs, oat hulls, cottonseed hulls, and bagasse. To this extent, the TMO-based zwitterionics are not based on scarce petrochemical feedstocks in the manner of ethylene oxide-containing surfactants. Nonetheless, the zwitterionic compounds used herein are somewhat expensive, relative to many "ordinary" detersive surfactants. By the practice of this invention, the TMO-zwitterionics can be blended with less expensive surfactants to provide compositions which exhibit superior cleaning performance at lower cost than compositions containing the TMO-zwitterionic as the sole surfactant, Moreover, desired suds levels, specialized cleaning uses, etc., can be provided by proper variations of the detersive surfactant. Finally, the optional use of builders in combination with the surfactant/TMO-zwitterionic co-surfactant mixtures herein allows the formulation of superior detergents for both fabric and hard surface cleaning at the most economical cost.

PRIOR ART

Various zwitterionic compounds have been suggested for use in both built and builder-free detergent compositions.

U.S. Pat. No. 3,684,427, to Walz, et al., issued Aug. 15, 1972, discloses alkoxylated zwitterionic surfactants and their use in fabric dyeing operations.

Belgian Pat. No. 813,502 to GAF Corporation, relates to di-ethoxylated quaternary ammonium compounds, phosphated or sulfated to form amphoteric surfactants. The compounds contain two alkylene oxide chains. U.S. Pat. No. 3,505,396, to H. L. Sanders, et al., issued Apr. 7, 1970, relates to sulfopropylated amphoteric surfactants containing ethylene oxide chains. U.S. Pat. No. 3,673,158, to A. M. Reader, et al., issued June 27, 1972, relates to sulfobetaine glycol modified with poly(ethylene terephthalate). U.S. Pat. No. 3,239,560, to C. M. Cambre, et al., issued Mar. 8, 1966, relates to the preparation of sulfobetaines having a hydroxy-substituted alkylene moiety interposed between the positive and negative charge centers of the surfactant-type molecules. U.S. Pat. No. 2,185,163, to H. Ulrich, issued Dec. 26, 1939, relates to alkoxylated derivatives of amine oxides containing anionic substituents. U.S. Pat. No. 2,115,250, to H. A. Bruson, issued Apr. 26, 1938, relates to alkoxylated amines and their salts and to the quaternary ammonium bases and salts derived from said amines. British Patent Specification 465,200, complete specification accepted Apr. 26, 1937, relates to quaternary ammonium or phosphonium, or tertiary sulfonium, compounds containing ether or polyether groups.

The co-pending application of Laughlin, Gosselink, Cilley, and Heuring, Ser. No. 493,951, filed Aug. 1, 1974, now U.S. Pat. No. 3,929,678 relates to zwitterionic surfactants having ethylene oxide moieties interposed between the cationic and anionic charge centers. The co-pending application of Laughlin, Gosselink, and Cilley, Ser. No. 493,956, filed Aug. 1, 1974, now abandoned relates to di-ethoxylated zwitterionic compounds having ethylene oxide groups interposed between the charge centers.

U.S. Pat. Nos. 3,668,240, issued June 5, 1972 and 3,764,568, issued Oct. 9, 1973, both to Barbera, disclose zwitterionic detergents having a 1,4-(2-butenylene) moiety between charge centers. See also U.S. Pat. No. 3,619,115, issued Nov. 9, 1971, to Diehl and Smith, which discloses zwitterionics in combination with builders and electrolytes. U.S. Pat. Nos. 3,452,066, issued June 24, 1969, and 2,781,390, issued Feb. 12, 1957, both to Mannheimer, broadly relate to various zwitterionic surfactants optionally containing a seemingly limitless variety of oxygen-containing, presumably hydrophilic, moieties, including alkylene oxides. U.S. Pat. No. 3,769,311, issued Oct. 30, 1973, to Armstrong and Dawald, discloses ethoxylated ammonio carboxylate zwitterionics, and describes compounds having limited ranges of ethyleneoxy and hydrophobic groups attached to the positive charge center. Also, Belgium Arrete 806,567 issued Oct. 29, 1973 to Recket and Colman Products, Ltd., discloses anionic ethoxylated amino sulfonates. (See also Japanese 3555 (1962), to Komori and Kashiwabara, Chem. Abstracts 53:4756e; British Pat. No. 1,296,351, complete specification published Nov. 15, 1972, to Cheng et al.; U.S. Pat. No. 3,178,366, issued Apr. 13, 1965, to Du Brow and Brandiff; U.S. Pat. No. 2,940,816, issued June 14, 1960, to Sniegowski; and German Application No. 1,159,957, filed Nov. 8, 1970 by Glabisch, et al., for other zwitterionic and/or quaternary ammonium compounds.)

The co-pending applications of Laughlin, et al., and Laughlin, et al., Ser. Nos. 493,952 and 493,953, each filed Aug. 1, 1974, now U.S. Pat. Nos. 3,928,262 and 3,929,678 relate to the use of ethoxylated zwitterionics with builders and/or auxiliary surfactants. The concurrently-filed application of Gosselink, et al., entitled DETERGENT COMPOUNDS, Ser. No. 562,307, filed Apr. 2, 1975, the disclosures of which are incorporated herein by reference, describes the TMO-based zwitterionic surfactants used in the instant compositions. The concurrently filed application of Wentler, entitled BUILT DETERGENT COMPOSITIONS, Ser. No. 562,310, filed Apr. 2, 1975, the disclosures of which are incorporated herein by reference, relates to the use of the TMO-zwitterionics herein in combination with builders.

SUMMARY OF THE INVENTION

This invention encompasses detergent compositions, comprising:
  a. a detersive amount (i.e., from about 1% to about 99%, preferably 6% to 50%, by weight) of a water-soluble detersive surfactant selected from non-ionic, anionic, semi-polar and non-TMO based zwitterionic surfactants;
  b. a detersive amount (i.e., from about 1% to about 99%, preferably 6% to 50%, by weight) of a water-soluble co-surfactant of the formula

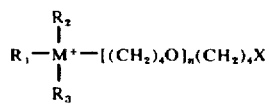

wherein $R_1$, $R_2$, $R_3$, M, X and $n$ are as defined below; and
  c. optionally, an effective amount (i.e., usually from about 5% to about 95%, more preferably 25% to 65%, by weight) of a detergency builder.

The balance of the compositions can comprise various detergency adjuncts, fillers, carriers, and the like, well-known in the detergency arts.

DETAILED DESCRIPTION OF THE INVENTION

The detergent compositions of this invention comprise a surfactant, a TMO-zwitterionic co-surfactant and, optionally, a detergency builder, which are described, in turn, below.

Surfactant

Water-soluble surfactants used in the present compositions include any of the common anionic, nonionic, semi-polar, or non-TMO-based zwitterionic (or ampholytic) detersive surface active agents well known in the detergent arts. Mixtures of such surface active agents can also be employed as the surfactant component of the present compositons. More particularly, the surfactants listed in U.S. Pat. Nos. 3,332,880 and 3,697,364, issued Sept. 26, 1972, to J. B. Edwards, each incorporated herein by reference, can be used herein. As will be disclosed more fully hereinafter, the nonionic surfactants are especially preferred for use with the TMO-zwitterionic co-surfactants.

Non-limiting examples of surfactants suitable for use in the instant compositions and processes are as follows.

Highly preferred surfactants herein comprise the typical nonionic surfactants well known in the detergency arts. Such surfactants can be generally described as the condensation products of an alkylene oxide (hydrophilic in nature), especially ethylene oxide (EO), with an organic hydrophobic compound, which is usually aliphatic or alkyl aromatic in nature. The length of the hydrophilic (i.e., polyoxyalkylene) moiety which is condensed with any particular hydrophobic compound can be readily adjusted to yield a water-soluble compound having the desired degree of balance between hydrophophilic and hydrophobic elements. Surprisingly, compositions comprising a nonionic surfactant and a TMO-based zwitterionic co-surfactant of the type disclosed herein provide detergency performance equivalent to fully-built detergents presently available commercially. Specific examples of suitable nonionic surfactants include the following.

The polyethylene oxide condensates of alkyl phenols are a well-known type of water-soluble ethoxylated nonionic surfactant. These compounds include the condensation products of alkyl phenols having an alkyl group containing from about 6 to 12 carbon atoms in either a straight chain or branched chain configuration, with ethylene oxide, said ethylene oxide being present in amounts equal to 5 to 25 moles of ethylene oxide per mole of alkyl phenol. The alkyl substituent in such compounds can be derived, for example, from polymerized propylene, diisobutylene, octene, or nonene. Examples of compounds of this type include nonyl phenol condensed with about 9.5 moles of ethylene oxide per mole of nonyl phenol; dodecyl phenol condensed with about 12 moles of ethylene oxide per mole of phenol; dinonyl phenol condensed with about 15 moles of ethylene oxide per mole of phenol; and di-isooctylphenol condensed with about 15 moles of ethylene oxide per mole of phenol. Commercially available nonionic surfactants of this type include Igepal CO-630, marketed by the GAF Corporation, and Triton X-45, X-114, X-100 and X-102, all marketed by the Rohm and Hass Company.

The condensation products of aliphatic alcohols with ethylene oxide are another (and highly preferred) type of nonionic surfactant used herein. The alkyl chain of the aliphatic alcohol can be either straight or branched, and generally contains from about 8 to about 22, preferably 10 to 16, carbon atoms. Examples of such ethoxylated alcohols include the condensation product of about 6 moles of ethylene oxide with 1 mole of tridecanol; myristyl alcohol condensed with about 10 moles of ethylene oxide per mole of myristyl alcohol; the condensation product of ethylene oxide with coconut fatty alcohol wherein the coconut alcohol is a mixture of fatty alcohols with alkyl chains varying from 10 to 14 carbon atoms in length and wherein the condensate contains about 6 moles of ethylene oxide per mole of alcohol; and the condensation product of about 9 moles of ethylene oxide with the above-described coconut alcohol. Tallow alcohol ethoxylates $(EO)_6$ to $(EO)_9$ are similarly useful herein. Examples of commercially available nonionic surfactants of the foregoing type include Tergitol 15-S-9, marketed by the Union Carbide Corporation; Neodol 23-6.5, marketed by the Shell Chemical Company; and Kyro EOB, marketed by The Procter & Gamble Company.

The condensation products of ethylene oxide with a hydrophobic base formed by the condensation of propylene oxide with propylene glycol constitute another type of nonionic surfactant. The hydrophobic portion of these compounds has a molecular weight of from about 1500 to 18000 and, of course, exhibits water insolubility. The addition of polyoxyethylene moieties to this hydrophobic portion tends to increase the water-solubility of the molecule as a whole, and the liquid character of the product is retained up to the point where the polyoxyethylene content is about 50% of the total weight of the condensation product. Examples of compounds of this type include certain of the commercially available Pluronic surfactants, marketed by BASF Wyandotte.

The condensation products of ethylene oxide with the product resulting from the reaction of propylene oxide and ethylene diamine are another type of nonionic surfactant used herein. The hydrophobic "base" of these condensation products consists of the reaction product of ethylene diamine and excess propylene oxide, said base having a molecular weight of from about 2500 to about 3000. This base compound is thereafter condensed with ethylene oxide to the extent that the condensation product contains from about 40 to about 80% by weight of polyoxyethylene and has a molecular weight of from about 5,000 to about 11,000. Examples of this type of nonionic surfactant include certain of the commercially available Tetronic compounds, marketed by BASF Wyandotte.

Other surfactants useful herein include the various well-known anionic surface active agents such as the soaps, the alkyl benzene sulfonates, alkyl sulfates, and the like. While combinations of anionic and TMO-based zwitterionic surfactants do not give the unexpectedly superior detergency performance exhibited by the nonionic/TMO-based zwitterionic mixtures disclosed above, such combinations do represent good detergents. Moreover, surfactants other than nonionics offer desirable sudsing and like characteristics, and can be used in combination with the TMO-based zwitterionics for this reason.

Water-soluble salts of the higher fatty acids, i.e., "soaps" are useful anionic surfactants herein. This class of surfactants includes ordinary alkali metal soaps such as the sodium, potassium, ammonium and alkanolammonium salts of higher fatty acids containing from about 8 to about 24 carbon atoms and preferably from about 10 to about 20 carbon atoms. Soaps can be made by direct saponification of fats and oils or by the neutralization of free fatty acids. Particularly useful are the sodium and potassium salts of the mixtures of fatty acids derived from coconut oil and tallow, i.e., sodium or potassium tallow and coconut soap.

Another class of anionic surfactants includes water-soluble salts, particularly the alkali metal, ammonium and alkanolammonium salts, of organic sulfuric reaction products having in their molecular structure an alkyl group containing from about 8 to about 22 carbon atoms and a sulfonic acid or sulfuric acid ester group. (Included in the term "alkyl" is the alkyl portion of acyl groups.) Examples of this group of synthetic surfactants which can be used in the present invention are the sodium and potassium alkyl sulfates, especially those obtained by sulfating the higher alcohols ($C_8$–$C_{18}$ carbon atoms) produced by reducing the glycerides of tallow or coconut oil; and sodium and potassium alkyl benzene sulfonates, in which the alkyl group contains from about 9 to about 15 carbon atoms, in straight chain or branched chain configuration, e.g., those of the type described in U.S. Pat. Nos. 2,220,099 and 2,477,383. Linear straight chain alkyl benzene sulfonates in which the average of the alkyl groups is about 13 carbon atoms, abbreviated as $C_{13}$LAS, as well as $C_{11.8(avg.)}$LAS are typically used.

Other anionic surfactant compounds herein include the sodium alkyl glyceryl ether sulfonates, especially those ethers of higher alcohols derived from tallow and coconut oil; sodium coconut oil fatty acid monoglyceride sulfonates and sulfates; and sodium or potassium salts of alkyl phenol ethylene oxide ether sulfate containing about 1 to about 10 units of ethylene oxide per molecule and wherein the alkyl groups containing about 8 to about 12 carbon atoms.

Other useful anionic surfactants herein include the water-soluble salts of esters of 60-sulfonated fatty acids containing from about 6 to 20 carbon atoms in the ester group; water-soluble salts of 2-acyloxy-alkane-1-sulfonic acids containing from about 2 to 9 carbon atoms in the acyl group and from about 9 to about 23 carbon atoms in the alkane moiety; alkyl ether sulfates containing from about 10 to 20 carbon atoms in the alkyl group and from about 1 to 30 moles of ethylene oxide; water-soluble salts of olefin sulfonates containing from about 12 to 24 carbon atoms; and $\beta$-alkyloxy alkane sulfonates containing from about 1 to 3 carbon atoms in the alkyl group and from about 8 to 20 carbon atoms in the alkane moiety.

Preferred water-soluble anionic organic surfactants herein include linear alkyl benzene sulfonates containing from about 11 to 14 carbon atoms in the alkyl group; the tallow range alkyl sulfates; the coconut range alkyl glyceryl sulfonates; alkyl ether (ethoxylated) sulfates wherein the alkyl moiety contains from about 14 to 18 carbon atoms and wherein the average degree of ethoxylation varies between 1 and 12; the sulfated condensation products of tallow alcohol with from about 3 to 12 moles of ethylene oxide; olefin sulfonates containing from about 14 to 16 carbon atoms; and soaps, as hereinabove defined.

Specific preferred anionic surfactants for use herein include: sodium linear $C_{10}$–$C_{18}$ alkyl benzene sulfonate; thiethanolamine $C_{10}$–$C_{18}$ alkyl benzene sulfonate; sodium tallow alkyl sulfate; sodium coconut alkyl glyceryl ether sulfonate; the sodium salt of a sulfated condensation product of a tallow alcohol with from about 3 to about 12 moles of ethylene oxide; and the water-soluble sodium and potassium salts of higher fatty acids containing 10 to 18 carbon atoms.

It is to be recognized that any of the foregoing anionic surfactants can be used separately herein or as mixtures.

Semi-polar surfactants useful herein include water-soluble amine oxides containing one alkyl moiety of from about 10 to 28 carbon atoms and 2 moieties selected from the group consisting of alkyl moieties and hydroxyalkyl moieties containing from 1 to about 3 carbon atoms; water-soluble phosphine oxides containing one alkyl moiety of about 10 to 28 carbon atoms and 2 moieties selected from the group consisting of alkyl moieties and hydroxyalkyl moieties containing from about 1 to 3 carbon atoms; and water-soluble sulfoxides containing one alkyl moiety of from about 10 to 28 carbon atoms and a moiety selected from the group consisting of alkyl and hydroxyalkyl moieties of from 1 to 3 carbon atoms.

Ampholytic surfactants include non-TMO derivatives of aliphatic or aliphatic derivatives of heterocyclic secondary and tertiary amines in which the aliphatic moiety can be straight chain or branched and wherein one of the aliphatic substituents contains from about 8 to 18 carbon atoms and at least one aliphatic substituent contains an anionic water-solubilizing group.

Zwitterionic surfactants include non-TMO derivatives of aliphatic quaternary ammonium, phosphonium and sulfonium compounds in which the aliphatic moieties can be straight or branched chain, and wherein one of the aliphatic substituents contains from about 8 to 18 atoms and one contains an anionic water solubilizing group.

Co-Surfactant

The TMO-zwitterionic co-surfactants used herein are molecules which can be visualized as being made up of four distinct parts. Referring to the foregoing formula, the TMO-zwitterionics comprises a hydrocarbon portion composed of groups $R_1$, $R_2$ and $R_3$, a cationic charge center, M, an anionic charge center, X, and a tetramethylene oxide moiety interposed between said cationic and anionic charge centers.

The hydrocarbon portion of the zwitterionic cosurfactants can comprise straight chain, branched chain, etc., alkyl or alkenyl moieties, or aryl or alkaryl moieties, all as more fully described hereinafter. It will be understood by those skilled in the detergency arts that the hydrocarbon groups $R_1$, $R_2$ and $R_3$ can contain other substituents, such as halogen, hydroxyl, alkoxyl, and the like.

The cationic charge center in the detersive zwitterionics is ammonium or phosphonium, with ammonium being preferred due to the availability of amine precursor compounds and the desirability of providing phosphorus-free compositions.

The anionic charge center, X, can be, for example, sulfonate, sulfate, phosphonate, and like negatively charged moieties well recognized in the detergency arts as useful for imparting water solubility to detersive surfactants. Compounds of the present type wherein X is sulfate or sulfonate are highly preferred from the standpoint of ease-of-manufacture and detergency performance when used as co-surfactants in the present compositions.

The TMO-zwitterionics are characterized by tetramethylene oxide moieties interposed between the cationic and anionic charge centers of the molecule. The degree of polymerization of the TMO moieties is designated in the formula by integer $n$, which, in general, is within the range from about 1 to about 20, preferably from about 1 to about 10.

More particularly, hydrocarbon groups $R_1$, $R_2$ and $R_3$ can be independently selected from $C_1$–$C_{30}$ alkyl or alkenyl moieties; aryl moieties, such as phenyl, naphthyl, and the like; alkaryl moieties having an alkyl group in the range of $C_1$ to about $C_{30}$; or two R groups can be joined to form a $C_4$–$C_6$ heteroring compound with M.

When selecting a detersive co-surfactant of the TMO-zwitterionic type, it will be appreciated that groups $R_1$, $R_2$ and $R_3$ should preferably be selected to provide sufficient hydrocarbon content that the hydrocarbon portion of the molecule has substantial hydrophobic character. (However, even those TMO-zwitterionics wherein the R groups are all relatively short-chain, i.e., $C_1$–$C_4$, do function usefully as co-surfactants herein, especially in light-duty cleaning.) More particularly, groups $R_1 + R_2 + R_3$, together, preferably contain at least about 12 carbon atoms, more preferably at least about 14 carbon atoms.

Based on the foregoing considerations regarding the total hydrocarbon content of the groups $R_1 + R_2 + R_3$, it will be recognized by those skilled in the detergency arts that the hydrophobic character in the TMO-zwitterionic co-surfactants for superior detergency performance is secured when, for example, group $R_1$ is a straight chain or branched chain $C_{10}$–$C_{30}$ alkyl or alkenyl moiety, or an alkaryl moiety having a $C_6$–$C_{24}$ alkyl group, and $R_2$ and $R_3$ are each independently selected from $C_1$–$C_4$ alkyl or alkenyl moieties. Compounds wherein groups $R_1$ and $R_2$ are each independently selected from $C_6$–$C_{21}$ alkyl or alkenyl moieties and alkaryl moieties having a $C_6$–$C_{15}$ alkyl group, and wherein $R_3$ is a $C_1$–$C_4$ alkyl or alkenyl moiety, also have sufficient hydrocarbon content that the molecule has substantial hydrophobic character, and these are also highly useful detersive co-surfactants. Compounds wherein $R_1$, $R_2$ and $R_3$ are each independently selected from $C_6$–$C_{16}$ alkyl or alkenyl moieties and alkaryl moieties having a $C_6$–$C_{10}$ alkyl group are also useful detersive co-surfactants.

Typical detersive co-surfactants herein include the TMO-based zwitterionic compounds wherein $R_1$ is a straight chain or a branched chain $C_{10}$–$C_{30}$ alkyl or alkenyl moiety, or an alkaryl moiety having a $C_6$–$C_{24}$ alkyl group (preferably $R_1$ is a $C_{14}$–$C_{22}$ alkyl moiety or alkaryl moiety having a $C_8$–$c_{16}$ alkyl group; more preferably $R_1$ is a $C_{14}$–$C_{20}$ alkyl moiety); $R_2$ and $R_3$ are each independently selected from $C_1$–$C_4$ alkyl or alkenyl moieties or hydroxy-substituted $C_1$–$C_4$ alkyl or alkenyl moieties (preferably $R_2$ and $R_3$ are each independently selected from $C_1$–$C_3$ alkyl moieties, especially methyl); X is sulfate or sulfonate; and n is an integer of at least 1 (preferably n in an integer from about 1 to about 10).

Other detersive TMO-zwitterionic co-surfactants are those wherein $R_1$ an $R_2$ are each independently selected from $C_6$–$C_{22}$ alkyl or alkenyl moieties and alkaryl moieties having a $C_6$–$C_{16}$ alkyl group (preferably $R_1$ and $R_2$ are each independently selected from $C_8$–$C_{16}$ alkyl moieties, most preferably $C_{10}$–$C_{14}$ alkyl moieties); $R_3$ is a $C_1$–$C_4$ alkyl or alkenyl, or $C_1$–$C_4$ hydroxy-substituted or alkenyl moiety (preferably $R_3$ is $C_1$–$C_3$ alkyl, especially methyl) the sum of $R_1 + R_2 + R_3$ carbon atoms being in the range from about 13 to about 50 (preferably in the range from about 14 to about 40); and wherein X and integer, $n$, are as defined immediately hereinabove.

Other representative detersive co-surfactants of the present type are those wherein groups $R_1$, $R_2$ and $R_3$ are each independently selected from $C_6$–$C_{16}$ alkyl or alkenyl moieties and alkaryl moieties having a $C_6$–$C_{10}$ alkyl group (perferably, $R_1$, $R_2$ and $R_3$ are each independently selected from $C_8$–$C_{16}$ alkyl moieties, more preferably $C_8$–$C_{16}$ alkyl) the sum of $R_1 + R_2 + R_3$ carbon atoms being in the range from about 18 to about 48 (preferably about 24 to about 36); and wherein X and integer, $n$, are as defined immediately hereinabove.

The synthesis of the TMO-zwitterionic compounds used herein is carried out using commercially available starting materials. A non-limiting example of one such general synthetic route is as follow.

According to procedures described in the literature, tetrahydrofuran is refluxed with thionyl chloride and sulfuric acid for ca. 72 hours to provide a polymeric TMO-based dichloride. Sodium hydride is reacted with 1,4-tetramethylene glycol (excess, as solvent) until hydrogen evolution ceases and then reacted with the above dichloride to provide the corresponding poly-TMO glycol. The glycol is thereafter tosylated in standard fashion with tosyl chloride to form the corresponding TMO ditosylate. The ditosylate is then reacted with a tertiary amine (or phosphine) to form the TMO-based amine tosylate. The amine tosylate is thereafter reacted with sodium sulfite to form the TMO-based zwitterionic sulfonate, which is purified on a mixed bed ($H^+$, $OH^-$ form) resin.

It will be appreciated that zwitterionic compounds of the general formula above can be prepared using any of a variety amines or phosphines. Moreover, zwitterionic compounds having any desired degree of polymerization ot the TMO moiety (n) can be prepared in the same general fashion.

The following illustrates the preparation of TMO-zwitterionics useful herein, but is not intended to be limiting thereof. Reaction precursors and products include, inter alia, the following, wherein the letter designation corresponds to that used in the experimental procedure.

1,9-dichloro-5-oxanonane (A)

1,14-dichloro-5,10-dioxatetradecane (B)

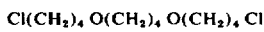

1,19-dihydroxy-5,10,15-trioxanonadecane (C)

1,24-dihydroxy-5,10,15,20-tetraoxatetracosane (D)

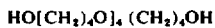

1,19-(5,10,15,-trioxanonadecylene)-bis(p-toluenesulfonate) (E)

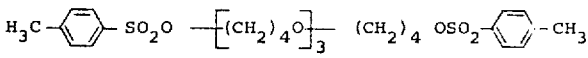

1,24-(5,10,15,20-tetraoxatetracosylene)-bis(p-toluenesulfonate) (F)

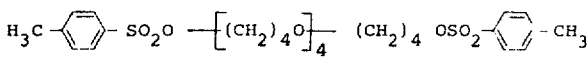

9-dimethyloctadecylammonio-5-oxanonane-1-sulfonate (G)

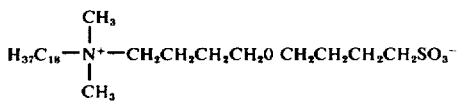

19-dimethyloctadecylammonio-5,10,15-trioxanonadecane-1-sulfonate (H)

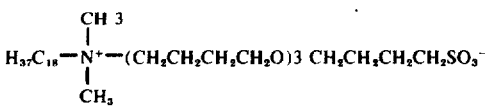

24-dimethyloctadecylammonio-5,10,15,20-tetraoxatetracosane-1-sulfonate (I)

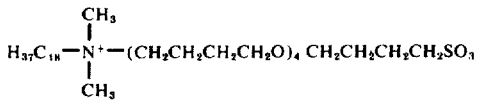

Preparation of 1,9-Dichloro-5-oxanonane (A) and 1,14-Dichloro-5,10-dioxatetradecane (B).

According to the chemistry of Reppe and Mitarbeiter, Ann 596, 38(1955), 15 g. of 95% sulfuric acid and 1 Kg. (13.9 mol) of thionyl chloride were added to 1.15 Dg. (16 mol) of dry tetrahydrofuran. This mixture was heated to reflux for 72 hrs; about 650 ml. of low boiling material (< 70° C) was then distilled and the residue fractionally distilled at low pressure. The first high boiling fraction gave 524 g. (2.6 mol) of title compound (A) (72° C/0.25 torr) and the second gave 212 g. (0.78 mol) of title compound (B) (145° C/0.6 torr).

Preparation of 1,19-Dihydroxy-5,10,15-Trioxanonadecane (C)

To 675 g. (7.5 mol) of 1,4-butanediol in a 3-neck, 2 flask fitted with a mechanical stirrer, thermometer, and argon inlet valve was added 46 g. (2.0 g-atoms) of freshly cut sodium. After stirring under argon at room temperature of 16 hrs. the temperature was raised to 80° C until the sodium had been consumed and hydrogen gas evolution had ceased. Two hundred thirty grams (1.15 mol) of dichloride (A) was then added dropwise over a four-hour period under argon, with stirring, and with the temperature at 80° C. This mixture was stirred under argon at 80° C for an additional 20 hrs. and until the reaction mixture was neutral to litmus. The mixture was cooled, the precipitated sodium chloride filtered and washed with ethanol, and the filtrate distilled from solid potassium carbonate that was added to the distillation pot. After removal of low boiling material, four fractions were obtained: 204 g. (2.26 mol) of 1,4-butanediol (88° C/0.6 torr), 24.6 g. (150° C/2.0 torr) of uninvestigated material, and 50.0 g. (197°-230° C/2.0 torr) of title compound (C), m.p. 22° C.

preparation of 1,24-dihydroxy-5,10,15,20-tetraoxatetracosane (D)

To 575 g. (6.4 mol) of 1,4-butanediol in a 2- , 3-neck flask fitted with a mechanical stirrer, thermometer, and argon inlet valve was added slowly 61.5 g. (1.28 mol) of hexane rinsed sodium hydride (50% in mineral oil). After hydrogen evolution had ceased, the reaction temperature was raised to 80° C and 173 g. (0.64 mol) of dichloride (B) was added dropwise. The mixture was stirred under argon at 80° C for 17 hrs. and for an additional 50 hrs. at 130°-140° C. The mixture was then cooled, the precipitated sodium chloride filtered and washed with ethanol, and the filtrate distilled at reduced pressure. After distillation of some low boiling material, 447 g. (495 mol) of 1,4-butanediol (88° C/0.6 torr) was distilled. The pot residue was crystallized from ether. Thin layer chromatography indicated an impurity was present. Continuous extraction of the liquid melt with hexanes for 3 days removed the impurity. Crystallization from a seeded ethereal solution afforded pure title compound (D), 179 g., m.p. 34.5°-36.5° C.

Preparation of 1,19-(5,10,15-Trioxanonadecylene)bis(p-Toluenesulfonate) (E)

To 61 g. (0.20 mol) of glycol (C) in 250 ml. (3.17 mol) of dry pyridine cooled to 0°–4° C was added in small portions 84 g. (0.44 mol) of tosyl chloride (i.e., p-toluene sulfonyl chloride). Addition of tosyl chloride, with stirring, was controlled so that the reaction temperature remained below 8° C. After stirring for 3 hrs. at 5° C, the reaction mixture was poured into a slurry of 1 liter of 12 N hydrochloric acid and 3 liters of ice. This mixture was extracted with three 500 ml-portions of chloroform. The combined extracts were washed with water, saturated sodium bicarbonate solution, dried ($Na_2SO_4$), and the solvent removed to yield the title ditosylate (E), 121 g., as a viscous oil.

Preparation of 1,24-(5,10,15,20-Tetraoxatetracosylene)bis(p-Toluenesulfonate) (F)

Forty grams (0.11 mol) of glycol (D) and 45 g. (0.23 mol) of tosyl chloride in 250 ml. (3.17 mol) of dry pyridine were allowed to react as in the preparation of E above. Evaporation of the solvent from the dried extract afforded 73 g. of product ditosylate (F) as a viscous oil.

Preparation of 9-Dimethyloctadecylammonio-5-oxanonane-1-sulfonate (G)

Twenty-five grams (0.126 mol) of dichloride (A) and 37 g. (0.126 mol) of distilled (b.p. 176°–179° C) dimethyloctadecylamine were heated at reflux in 150 ml of dry acetonitrile, with stirring, for 16 hrs. The solvent was then removed and the residue dissolved in 500 ml. of water. Fifty grams (0.40 mol) of sodium sulfite were added and the reaction mixture was refluxed until all dichloride (A) had been consumed as determined by thin layer chromatography. The mixture was then cooled, and extracted with three 200 ml-portions of chloroform. The combined extracts were dried ($Na_2SO_4$), the solvent evaporated, and the residue dissolved in methanol.

The above methanol solution was stirred with 400 g. of a mixed bed ion exchange resin (Rexyn 300 H—OH, commercially available from the Fisher Scientific Company) for 5 hrs. The resin was then filtered and the methanol solution concentrated to yield 19 g. of title compound (G) m.p. 114°–116° C.

The foregoing procedure is modified by replacing the $C_{18}H_{37}(CH_3)_2N$ with an equivalent amount of n—$C_{10}H_{21}(CH_3)_2N$, n—$C_{12}H_{25}(CH_3)_2N$, n—$C_{14}H_{29}(CH_3)_2N$, n—$C_{16}H_{33}(CH_3)_2N$ and n—$C_{20}H_{21}(CH_3)_2N$, respectively, and the corresponding dimethylammonio compounds wherein $R_1$ is, respectively, n—$C_{10}$; n—$C_{12}$; n—$C_{14}$; n—$C_{16}$; and n—$C_{20}$ are secured.

Preparation of 19-Dimethyloctadecylammonio-5,10,15-trioxanonadecane-1-sulfonate (H)

To 58 g. (0.096 mol) of ditosylate (E) in 150 ml. of dry acetonitrile was added 28 g. (0.096 mol) of distilled (b.p. 176°–179° C) dimethyloctadecylamine. This mixture was heated to reflux under argon, with stirring, for 16 hrs. The solvent was then removed and the residue dissolved in 500 ml. of methanol. Thirty-six grams (0.29 mol) of sodium sulfite in 500 ml. of water were added to the methanolic solution and this mixture was heated to reflux until thin layer chromatography indicated the absence of ditosylate (E). Additional methanol was added and the insoluble salts were filtered. The solvents were removed, the residue dissolved in methanol, and the methanolic solution purified with mixed bed resin, as above. Filtration of the resin and evaporation of the solvent afforded 15 g. of the title compound (H), m.p. 24° C.

In the foregoing procedure, the dimethyloctadecylamine is replaced by an equivalent amount of dimethyldodecylphosphine, didecylmethylphosphine and trioctylphosphine, respectively. The compounds wherein $R_1$ is dodecyl and $R_2$ and $R_3$ are each methyl; and wherein $R_1$, $R_2$ and $R_3$ are each octyl, are secured, respectively.

Preparation of 24-Dimethyloctadecylammonio-5,10,15,20-tetraoxatetracosane-1-sulfonate (I)

Fifty grams (0.073 mol) of ditosylate (F) and 22 g. (0.073 mol) of distilled (b.p. 176°–179° C) dimethyloctadecylamine were allowed to react as in the preparation of (H), above. After removal of the solvent, the residue was allowed to react with 27 g. (0.21 mol) of sodium sulfite in one liter of aqueous methanol (1:1,v/v) at reflux temperatures. After purification, as in the preparation of (H), above, the compound was crystallized from 1:1 ethyl acetate-chloroform and vacuum dried to yield 12 g. of the title compound (I), m.p. 61° C.

In the foregoing procedure, the dimethyloctadecylamine is replaced by an equivalent amount of dimethylbutyl amine and the corresponding sulfonate (wherein $R_1$ is butyl and $R_2$ and $R_3$ are each methyl) is secured.

In the foregoing procedure, the dimethyloctadecylamine is replaced by an equivalent amount of dioctylmethylamine and the corresponding sulfonate (wherein $R_1$ and $R_2$ are each octyl and $R_3$ is methyl) is secured.

In the foregoing procedure the dimethyloctadecylamine is replaced by an equivalent amount of $(C_{10}H_{21})_3N$ and the corresponding sulfonate (wherein $R_1$, $R_2$ and $R_3$ are each decyl) is secured.

Preparation of 19-Dimethyloctadecylammonio-5,10,15-Trioxanonadecane-1-Sulfate To 61 g (0.20 mol) of glycol (C) in 250 ml (3.17 mol) of dry pyridine cooled to 0.4° C is added in small portions 38 g (0.20 mol) of tosyl chloride as in the preparation of E. Purification and removal of solvent as in the preparation E affords a mixture of C, E, and the monotosylate of C. This mixture in 150 mls. of dry acetonitrile with 0.20 mol of dimethyloctadecylamine is heated to reflux in the manner disclosed above, and the solvent stripped on a rotary evaporator.

The mixture of material prepared in the foregoing manner is dissolved in 250 mls. of dry pyridine and cooled to 0°–5° C. Chlorosulfonic acid, 56 g (0.48 mol), dissolved in 250 ml of chloroform, is added dropwise to maintain the reaction temperature below 15° C. After addition of the chlorosulfonic acid, the mixture is stirred at 0° C for 1 hr., and at room temperature for an additional hour.

Following the reaction with the chlorosulfonic acid, the chloroform is vacuum-stripped. The semi-solid residue is poured into cooled 50% aqueous NaOH and extracted three times with chloroform. The combined extracts are purified with mixed bed resin (Rexyn 300 H—OH) to yield the title compound.

In the foregoing procedure, the n—$C_{18}H_{37}(CH_3)_2N$ is replaced by an equivalent amount of n—$C_{10}H_{21}(CH_3)_2N$, n—$C_{12}H_{25}(CH_3)_2N$, n—$C_{14}H_{29}(CH_3)_2N$, n—$C_{16}H_{33}(CH_3)_2N$, n—$C_{16}H_{31}(CH_3)_2N$, and n—$C_{20}H_{41}(CH_3)_2N$, respectively. The corresponding dimethylammonio sulfates wherein $R_1$ is decyl, dodecyl, tetradecyl, hexadecyl, hexadecenyl and eicosyl are secured, respectively.

In the foregoing procedure, the dimethyloctadecylamine is replaced by an equivlent amount of the following phosphines, respectively: dimethyldodecylphosphine; dimethyloctadecylphosphine; tris(decyl)phosphine; tritetradecylphosphine; and didodecylmethylphosphine. The corresponding phosphonium 5,10,15-trioxanonadecane sulfates are secured in each instance.

Preparation of 24-Dimethyloctadecylammonio-5,10,15,20-Tetraoxatetracosane-1-hydrogen Phosphonate To 40 g (0.11 mol) of glycol (D) in 100 ml of dry dimethylformamide is added 62 g (0.30 mol) of thionyl bromide. This mixture is heated until the conversion of the glycol to the dibromocompound is complete, and then neutralized with base. This neutralized mixture is extracted with chloroform, the extracts dried ($Na_2SO_4$), and the solvent removed to yield the dibromoderivative of D.

The material prepared above is then heated not higher than 130° C with 21 g (0.10 mol) of isopropylphosphite as 2-bromopropane distills. After the 2-bromopropane has all distilled, the reaction pressure is reduced to about 1 torr., whereupon additional low boiling distillates are removed.

The residue from the distillation above is cooled and chromatographed on silica gel to isolate the diisopropyl bromophosphonate. This purified monoester is allowed to react with an equal mole amount of dimethyloctadecylamine in refluxing acetonitrile in the manner disclosed above, and the solvent removed. This quaternary ammonium phosphonate ester is hydrolyzed with 3–6 N hydrochloroic acid to yield, after purification and solvent removal, the title compound.

Detergency Builder

The instant compositions optionally contain a detergency builder, and all manner of detergency builders commonly taught for use in detergent compositions are useful in combination with the present surfactant-/cosurfactant compositions. More specifically, the detergent compositions herein can contain from about 0 to about 95%, most preferably from about 15 to about 65%, by weight of said builders. Useful builders herein include any of the conventional inorganic and organic water-soluble builder salts, as well as various water-insoluble and so-called "seeded" builders.

Inorganic detergency builders useful herein include, for example, water-soluble salts of phosphates, pyrophosphates, orthophosphates, polyphosphates, silicates, carbonates, and the like. Organic builders include various water-soluble phosphonates, polyphosphonates, polyhydroxysulfonates, polyacetates, carboxylates, polycarboxylates, succinates, and the like.

Specific examples of inorganic phosphate builders include sodium and potassium tripolyphosphates, phosphates, and hexametaphosphates. The organic polyphosphonates specifically include, for example, the sodium and potassium salts of ethylene diphosphonic acid, the sodium and potassium salts of ethane 1-hydroxy-1,1-diphosphonic acid and the sodium and potassium salts of ethane-1,1,2-triphosphonic acid. Examples of these and other phosphorus builder compounds are disclosed in U.S. Pat. Nos. 3,159,581; 3,213,030; 3,422,021; 3,422,137; 3,400,176 and 3,400,148, incorporated herein by reference. Sodium tripolyphosphate is an especially preferred, water-soluble inorganic builder herein.

Non-phosphorus containing sequestrants can also be selected for use herein as detergency builder.

Specific examples of non-phosphorus, inorganic builder ingredients include water-soluble inorganic carbonate, bicarbonate, and silicate salts. The alkali metal, e.g., sodium and potassium carbonates, bicarbonates, and silicates are particularly useful herein.

Water-soluble, organic builders are also useful herein. For example, the alkali metal, ammonium and substituted ammonium polyacetates, carboxylates, polycarboxylates and polyhydroxysulfonates are useful builders in the present compositions and processes. Specific examples of the polyacetate and polycarboxylate builder salts include sodium, potassium lithium, ammonium and substituted ammonium salts of ethylenediaminetetraacetic acid, nitrilotriacetic acid, oxydisuccinic acid, mellitic acid, benzene polycarboxylic (i.e., penta- and tetra-) acids, and citric acid.

Highly preferred non-phosphorus builder materials (both organic and inorganic) herein include sodium carbonate, sodium bicarbonate, sodium silicate, sodium citrate, sodium oxydisuccinate, sodium mellitate, sodium nitrilotriacetate, and sodium ethylenediaminetetraacetate, and mixtures thereof.

Other highly preferred organic builders herein are the polycarboxylate builders set forth in U.S. Pat. No. 3,308,067, Diehl, incorporated herein by reference. Examples of such materials include the water-soluble salts of homo- and co-polymers of aliphatic carboxylic acids such as maleic acid, itaconic acid, mesaconic acid, fumaric acid, aconitric acid, citraconic acid and methylenemalonic acid.

Additional, preferred builders herein include the water-soluble salts, especially the sodium and potassium salts, of carboxymethyloxymalonate, carboxymethyloxysuccinate, cis-cyclohexanehexacarboxylate, cis-cyclopentanetetracarboxylate and phloroglucinol trisulfonate.

Sodium nitrilotriacetate is an especially preferred, water-soluble organic builder herein.

Another type of detergency builder material useful in the present compositions and processes comprises a water-soluble material capable of forming a water-insoluble reaction product with water hardness cations in combination with a crystallization seed which is capable of providing growth sites for said reaction product. Such "seeded builder" compositions are fully disclosed in the co-pending application of Benjamin, Ser. No. 248,546, filed Apr. 28, 1972, the disclosures of which are incorporated herein by reference.

More particularly, the seeded builders useful herein comprise a crystallization seed having a maximum particle dimension of less than 20 microns, preferably a particle diameter of from about 0.001 micron to about 5 microns, in combination with a material capable of forming a water-insoluble reaction product with free metal ions.

Many builder materials, e.g., the water-soluble carbonate salts, precipitate water hardness cations, thereby performing a builder function. Unfortunately, many of the precipitating builders used in detergent compositions do not reduce the free metal ion content of laundry baths quickly, and such builders only compete with the organic detergent and the soil for the free metal ions. The result is that while some of the free metal ions are removed from the solution, some ions do react with the organic detergent and the soil, thereby decreasing the detersive action. The use of the crystallization seed quickens the rate of precipitation of the metal hardness, thereby removing the hardness ions before they can adversely affect the detergency performance.

By using a material capable of forming a water-insoluble product with free metal ions in combination with a crystallization seed, the combined free metal ion concentration of an aqueous laundering liquor can be reduced to less than 0.5 grains of hardness within about 120 seconds. In fact, the preferred seeded builders can reduce the free metal hardness to less than 0.1 grains/gallon within about 30 seconds.

Preferred seeded builders consist of: a water-soluble material capable of forming a reaction product having a solubility in water of less than about $1.4 \times 10^{-2}$ wt. % (at 25° C) with divalent and polyvalent metal ions such as calcium, magnesium and iron; and a crystallization seed (0.001–20 micron diameter) which comprises a material which will not completely dissolve in water within 120 seconds at 25° C.

Specific examples of materials capable of forming the water-insoluble reaction product include the water-soluble salts of carbonates, bicarbonates, sesquicarbonates, silicates, aluminates and oxalates. The alkali metal, especially sodium, salts of the foregoing materials are preferred for convenience and economy.

The crystallization seed employed in such seeded builders is preferably selected from the group consisting of calcium carbonate; calcium and magnesium oxalates; barium sulfate; calcium, magnesium and aluminum silicates; calcium and magnesium oxides; calcium and magnesium salts of fatty acids having 12 to 22 carbon atoms; calcium and magnesium hydroxides; calcium fluoride; and barium carbonate. Specific examples of such seeded builder mixtures comprise: 3:1 wt. mixtures of sodium carbonate and calcium carbonate having a 5 micron particle diameter; 2.7:1 wt. mixtures of sodium sesquicarbonate and calcium carbonate having a particle diameter of 0.5 microns; 20:1 wt. mixtures of sodium sesquicarbonate and calcium hydroxide having a particle diameter of 0.01 micron; and a 3:3:1 wt. mixture of sodium carbonate, sodium aluminate and calcium oxide having a particle diameter of 5 microns.

A seeded builder comprising a mixture of sodium carbonate and calcium carbonate is especially preferred herein. A highly preferred seeded builder comprises a 30:1 to 5:1 (wt. $Na_2CO_3$:$CaCO_3$) mixture of sodium carbonate and calcium carbonate wherein the calcium carbonate has an average particle diameter from 0.01 micron to 5 microns.

Another type of builder useful herein includes various substantially water-insoluble materials which are capable of reducing the hardness content of laundering liquors, e.g., by ion-exchange processes. Examples of such builder materials include tthe phosphorylated cloths disclosed in U.S. Pat. No. 3,424,545, to R. A. Bauman, issued Jan. 28, 1969, incorporated herein by reference.

The complex aluminosilicates, i.e., zeolite-type materials, are another type of substantially water-insoluble builder useful in the present compositions, and these materials readily soften water, i.e., remove $Ca^{++}$ hardness. Both the naturally occurring and synthetic "zeolites," especially the zeolite A and hydrated zeolite A materials, are useful for this builder/softener purpose. A description of zeolite A materials and a method of preparation appears in U.S. Pat. No. 2,882,243, entitled MOLECULAR SIEVE ADSORBENTS, issued Apr. 14, 1959, incorporated herein by reference.

Optional Ingredients

The compositions herein can contain all manner of detergent adjunct materials and carriers commonly found in laundering and cleaning compositions. For example, various perfumes, optical bleaches, fillers, anti-caking agents, fabric softeners and the like can be present to provide the usual benefits occasioned by the use of such materials in detergent compositions.

Perborate bleaches commonly employed in European detergent compositions can also be present as a component of the instant detergent compositions, and are added thereto as dry admixes.

Enzymes, especially the thermally stable proteolytic and lipolytic enzymes used in laundry detergents, can be dry-mixed in the compositions herein.

Materials such as sodium sulfate can be used as fillers for the granular compositions herein. Water and water-alcohol mixtures (especially 20:1 to 10:1 wt. water/ethanol mixtures) are useful carriers for liquid compositions comprising the surfactant, TMO-based zwitterionic cosurfactant and optional builders disclosed herein.

The following examples illustrate the practice of this invention but are not intended to be limiting thereof.

EXAMPLE I

A liquid detergent composition comprising a nonionic surfactant and a TMO-based zwitterionic cosurfactant is as follows.

| Ingredient | % (wt.) |
|---|---|
| Neodol 45/7* | 20 |
| Compound I** | 20 |
| Water-ethanol (90:10 wt.) | Balance |

*Mixed $C_{14}$–$C_{15}$ alcohols ethoxylated to an average degree of 7 EO groups.
**24-dimethyloctadecylammonio-5,10,15,20-tetraoxatetra-cosane-1-sulfonate, Compound I prepared hereinabove.

The composition of Example I is prepared by simply mixing the ingredients in the indicated proportions.

The composition of Example I is used at a concentration of ca. 0.25 cup in 20 gallons of water to launder fabrics heavily stained with clay soil and various oily and food stains. Used at this concentration, the composition of Example I delivers detergency performance equal to, or better than, the detergency performance of fullybuilt, commercially available, granular detergents.

The composition of Example I is used at a concentration which provides 125 ppm of the nonionic surfactant and 125 ppm of the zwitterionic co-surfactant in an aqueous laundering bath. A bath comprising 250 ppm of the Compound I, without added nonionic, is used to launder similarly stained fabrics. In this test, the bath containing the nonionic surfactant plus TMO-based co-surfactant exhibits equivalent, or better, overall detergency performance to the bath containing the all-TMO-zwitterionic.

In the composition of Example I, Compound 1 is replaced by an equivalent amount of Compound G and Compound H, respectively, and excellent detergency performance is secured.

In the composition of Example I, the Neodol 45/7 nonionic surfactant is replaced by an equivalent amount of coconut alcohol $(EO)_8$, tallow alcohol $(EO)_9$, the condensation product of 6 moles of ethylene oxide with 1 mole of tridecanol, and the condensation product of about 9.5 moles of ethylene oxide with nonylphenol, respectively, and excellent oily and clay soil fabric detergency performance is secured.

Preferred compositions herein comprise the surfactant and the TMO zwitterionic co-surfactant at a weight ratio from about 1:5 to about 5:1. Highly preferred are compositions wherein the surfactant is nonionic and the surfactant/co-surfactant weight ratio is ca. 1:3 to 3:1. Most preferred compositions comprise nonionic surfactant/co-surfactant mixtures at about a 1:1 weight ratio. The following example illustrates the use of laundry baths containing compositions within these ratios to secure excellent detergency performance. The economic advantage secured by using the relatively inexpensive nonionic surfactant with the relatively expensive TMO zwitterionic, rather than compositions comprising all-TMO zwitterionic as the sole detersive ingredient, and without loss of performance is an important consideration to detergent manufacturers.

EXAMPLE II

An aqueous laundry bath containing 250 ppm of Compound I, prepared hereinabove, 300 ppm of Neodol 45/7, 25 ppm of triethanolamine, and 100 ppm ethanol is prepared. Cotton, polyester/cotton and pure polyester fabrics, each heavily stained with clay soil, are placed in the bath and laundered in standard fashion. Following this treatment, the fabrics are rinsed and dried. Clay soil removal from the fabrics is fully equivalent to, or better than, that secured when similarly stained fabrics are laundered in a commercial, phosphate-built detergent composition according to the detergent manufacturer's instructions.

In the foregoing procedure, the concentration of Compound I is reduced to 125 ppm and excellent detergency performance (averaging about 90% of that secured with the commercial built detergent, approximated over three fabric types) is secured.

As can be seen from the foregoing examples, the compositions herein comprising a nonionic surfactant and a TMO-based co-surfactant provide excellent detergency performance. When anionic surfactants such as the alkyl benzene sulfonates are included in such compositions, some diminution in clay removal performance, especially on pure polyester fabrics, is seen. However, the other desirable cleaning attributes and sudsing performance of anionic surfactants such as the alkyl benzene sulfonates often makes it desirable to include such materials in the compositions. Moreover, it is to be understood that compositions formulated with anionic surfactants and the TMO-based co-surfactants herein do provide quite good detergency performance; however, the truly outstanding clay soil removal of mixtures comprising the nonionic surfactant and co-surfactant is not fully achieved.

The following example is typical of a fully formulated, built detergent composition of the present type which provides excellent detergency performance over a variety of fabrics and soil types, and which exhibits sudsing properties familiar and acceptable to users of granular detergents.

EXAMPLE III

| Ingredient | % (wt.) |
|---|---|
| Neodol 45/7 | 12.5 |
| Compound I | 12.5 |
| $C_{11.8}$ alkyl benzene sulfonate, sodium form | 7.5 |
| Sodium tripolyphosphate | 20.0 |
| Sodium silicate (water-soluble) | 5.0 |
| Sodium sulfate | 39.0 |
| Water | Balance |

The composition of Example III is prepared by a dry-mixing procedure. In a typical procedure, the liquid Neodol nonionic surfactant is sorbed onto and into the granules of sodium sulfate and sodium tripolyphosphate. Thereafter, all ingredients are thoroughly blended to provide a homogeneous, powdered composition.

One cup of the composition of Example III is employed in 20 gallons of hot (115° F) water to launder a 10-pound load of mixed cotton, polyester/cotton and polyester fabrics in a top-loading automatic washing machine according to manufacturer's instructions. The washing cycle is ca. 10 minutes. During the washing cycle, foam height is found to be at an acceptable level. After rinsing and drying in an automatic dryer, the fabrics are substantially free from oily (including body oils) and particulate soils.

In the composition of Example III, the sodium tripolyphosphate builder is replaced by an equivalent amount of hydrated zeolite A (avg. particle diameter ca. 1 micron) and good overall detergency is secured.

What is claimed is:

1. A detergent composition, consisting essentially of:
   a. from about 1% to about 99% by weight of a water-soluble detersive surfactant selected from nonionic, anionic, semi-polar and non-TMO based zwitterionic surfactants;
   b. from about 1% to about 99% by weight of a water-soluble co-surfactant of the formula:

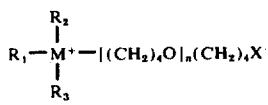

wherein $R_1$, $R_2$ and $R_3$ are independently selected from $C_1$ to $C_{30}$ alkyl or alkenyl moieties, aryl moieties, alkaryl moieties having an alkyl group in the range of $C_1$ to $C_{30}$, or wherein two R moieties are joined to form a $C_4$ to $C_6$ heteroring with M; M is nitrogen or phosphorus; n is an integer from 1 to about 20; and X is a watersolubilizing anionic moiety; and
   c. from about 0% to about 95% by weight of a detergency builder.

2. A composition according to claim 1 wherein the water-soluble detersive surfactant and the water-soluble co-surfactant each represent from about 6 to about 50% by weight of the composition.

3. A composition according to claim 1 wherein the surfactant is a nonionic surfactant.

4. A composition according to claim 3 wherein the nonionic surfactant is the condensation product of ethylene oxide with an organic hydrophobic compound.

5. A composition according to claim 4 wherein the nonionic surfactant is selected from the condensation products of ethylene oxide with hydrophobic compounds selected from alkyl phenols, aliphatic alcohols, condensation products of propylene oxide and propylene glycol, and condensation products of propylene oxide and ethylene diamine.

6. A composition according to claim 5 wherein the nonionic surfactant is selected from $C_8-C_{22}$ aliphatic alcohols condensed with from about 6 to about 9 moles of ethylene oxide per mole of alcohol, and mixtures thereof.

7. A composition according to claim 1 wherein the surfactant is an anionic surface active agent selected from soaps, alkyl sulfates, alkyl benzene sulfonates, alkyl glyceryl ether sulfonates, and ethoxylated alkyl ether sulfates.

8. A composition according to claim 1 wherein X is sulfate or sulfonate.

9. A composition according to claim 8 wherein $R_1 + R_2 + R_3$, together, contain at least about 12 carbon atoms.

10. A composition according to claim 9 wherein $R_1$ is a straight chain or branched chain $C_{10}-C_{30}$ alkyl or alkenyl moiety, or an alkaryl moiety having $C_6-C_{24}$ alkyl group, and wherein $R_2$ and $R_3$ are each independently selected from $C_1-C_4$ alkyl or alkenyl moieties or hydroxysubstituted $C_1-C_4$ alkyl or alkenyl moieties.

11. A composition according to claim 10 wherein $R_1$ is a $C_{14}-C_{22}$ alkyl moiety or alkaryl moiety having a $C_8-C_{18}$ alkyl group, $R_2$ and $R_3$ are each methyl, M is nitrogen, and n is an integer in the range from 1 to about 10.

12. A composition according to claim 11 wherein the co-surfactant is selected from 9-dimethyloctadecylammonio-5-oxoanonane-1-sulfonate, 19-dimethylocatadecylammonio-5,10,15-trioxanonadecane-1-sulfonate, 24-dimethyloctadecylammonio-5,10,15,20-tetraoxatetracosane-1-sulfonate, 19-dimethyloctadecylammonio-5,10,15-trioxanonadecane-1-sulfate, or mixtures thereof.

13. A composition according to claim 9 wherin $R_1$ and $R_2$ are each independently selected from $C_6-C_{22}$ alkyl or alkenyl moieties or alkaryl moieties having a $C_6-C_{16}$ alkyl group and wherein $R_3$ is a $C_1-C_4$ alkyl or alkenyl moiety or hydroxy-substituted $C_1-C_4$ alkyl or alkenyl moiety.

14. A composition according to claim 13 wherein $R_1$ and $R_2$ are each selected from $C_8-C_{16}$ alkyl moieties, $R_3$ is methyl, M is nitrogen, and n is an integer in the range of from 1 to about 10.

15. A composition according to claim 9 wherein $R_1$, $R_2$ and $R_3$ are each independently selected from $C_6-C_{16}$ alkyl or alkenyl moieties or alkaryl moieties having a $C_6-C_{10}$ alkyl group.

16. A composition according to claim 15 wherein $R_1$, $R_2$ and $R_3$ are each independently selected from $C_8-C_{16}$ alkyl moieties, the sum of $R_1 + R_2 + R_3$ carbon atoms being in the range from about 24 to about 48, M is nitrogen, and n is an integer in the range from 1 to about 10.

17. A composition according to claim 1 wherein the weight ratio of surfactant:co-surfactant is in the range of about 1:5 to about 5:1.

18. A composition according to claim 17 wherein the surfactant is nonionic.

19. A composition according to claim 18 wherein the nonionic surfactant:co-surfactant ratio is in the range of about 1:3 to about 3:1.

20. A composition according to claim 19 wherein the nonionic surfactant is ethylene oxide condensed with an organic hydrophobic compound.

21. A composition according to claim 20 wherein the organic hydrophobic compound is an aliphatic alcohol, an alkyl phenol, or mixtures thereof.

22. A composition according to claim 1 wherein there is present from about 15 to about 65% by weight of a water-soluble detergency builder.

23. A composition according to claim 22 wherein the builder is an inorganic detergency builder.

24. A composition according to claim 23 wherein the inorganic builder is sodium tripolyphosphate.

25. A composition according to claim 22 wherein the builder is an organic detergency builder.

26. A composition according to claim 25 wherein the organic builder is sodium nitrilotriacetate.

27. A composition according to claim 1 wherein there is present from about 15 to about 65% by weight of a seeded detergency builder.

28. A composition according to claim 27 wherein the seeded builder comprises a 30:1 to 5:1 weight mixture of sodium carbonate and particulate calcium carbonate having an average particle diameter of 0.01 micron to 5 microns.

29. A composition according to claim 1 wherein there is present from about 15 to about 65% by weight of a substantially water-insoluble detergency builder.

30. A composition according to claim 29 wherein the detergency builder is a zeolite-type material.

* * * * *